(12) United States Patent
Hirshfeld

(10) Patent No.: US 6,425,398 B1
(45) Date of Patent: Jul. 30, 2002

(54) EARPLUG

(76) Inventor: Eallan Hirshfeld, 37 Herzl Street, Ra'anana 43353 (IL)

(*) Notice: Subject to any disclaimer, the term of this patent is extended or adjusted under 35 U.S.C. 154(b) by 0 days.

(21) Appl. No.: 09/701,983

(22) PCT Filed: Jun. 8, 1999

(86) PCT No.: PCT/IL99/00308

§ 371 (c)(1),
(2), (4) Date: Dec. 6, 2000

(87) PCT Pub. No.: WO99/63918

PCT Pub. Date: Dec. 16, 1999

(30) Foreign Application Priority Data

| Jun. 11, 1998 | (IL) | ................................ 124864 |
| Jan. 24, 1999 | (IL) | ................................ 128208 |

(51) Int. Cl.$^7$ .............................................. A61F 11/00
(52) U.S. Cl. ......................... 128/864; 128/865; 128/867
(58) Field of Search ........................ 128/846, 864–868; 181/130, 131, 135

(56) References Cited

U.S. PATENT DOCUMENTS

| 2,487,038 A | * | 11/1949 | Baum ........................... 128/867 |
| 2,619,960 A | * | 12/1952 | Reynolds ..................... 128/868 |
| 3,565,069 A | * | 2/1971 | Miller .......................... 128/867 |
| 3,842,829 A | * | 10/1974 | Ellis ............................. 128/868 |
| 3,872,559 A | | 3/1975 | Leight |
| 4,055,233 A | | 10/1977 | Huntress |
| 4,094,315 A | | 6/1978 | Leight |
| 4,540,063 A | | 9/1985 | Ochi et al. |
| 6,068,079 A | * | 5/2000 | Hamery ....................... 128/868 |

FOREIGN PATENT DOCUMENTS

| DE | 1120632 | 11/1960 |
| DE | 1947740 | 5/1971 |
| DE | 4217043 | 11/1992 |
| DE | 9411651 | 9/1994 |
| EP | 0995025 | 11/1999 |
| FR | 1036458 | 9/1953 |
| GB | 643927 | 9/1950 |
| WO | WO 9936016 | 7/1999 |

* cited by examiner

Primary Examiner—Michael A. Brown
(74) Attorney, Agent, or Firm—Eitan, Pearl, Latzer & Cohen-Zedek

(57) ABSTRACT

An earplug (20) is provided which allows conversation to be conducted whilst inserted in the ear, and blocks out certain noise without substantially sealing the ear canal, and causing discomfort to the wearer. In one embodiment, the earplug includes a first cylindrical element (28) open at one end (30), having a substantially convex shape at its other end (34) for insertion into the outer ear canal, and a second element (32) which fits into the open end of the first cylindrical element to form a connecting juncture therewith. The first and second elements have air circulation means.

31 Claims, 4 Drawing Sheets

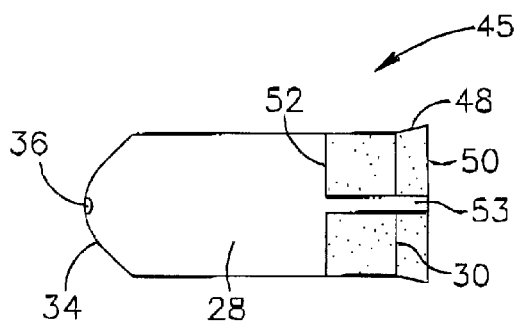
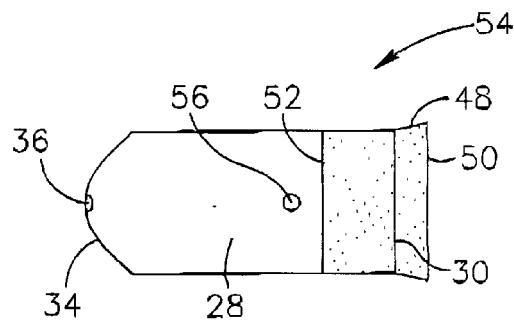
FIG.4A  FIG.4B
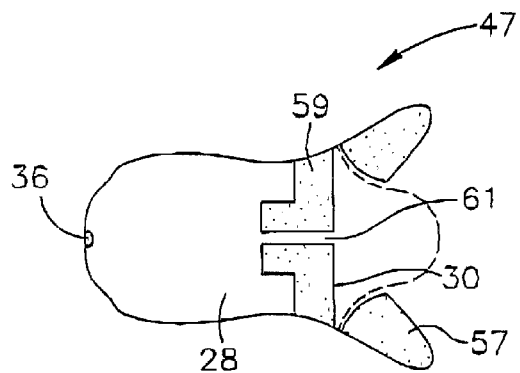
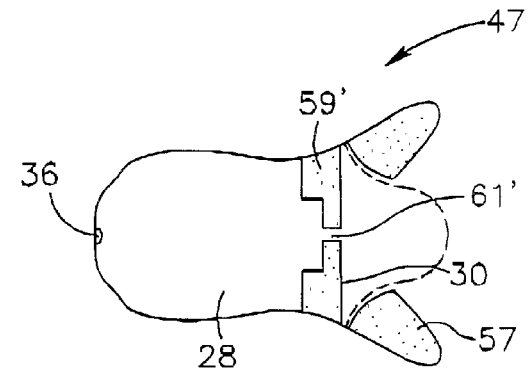
FIG.4C  FIG.4D
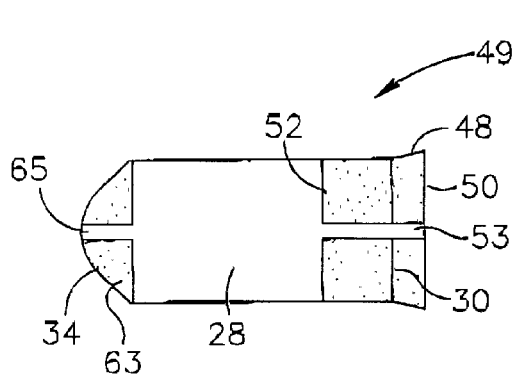
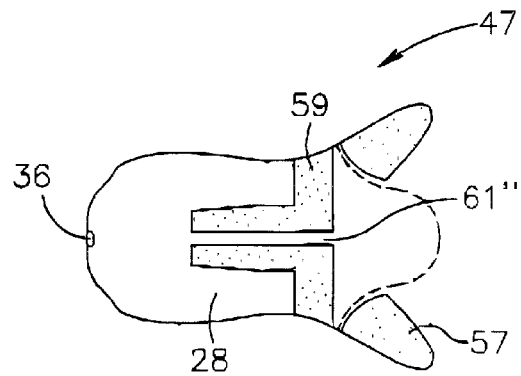
FIG.4E  FIG.4F

EARPLUG

FIELD OF THE INVENTION

The present invention relates to earplugs generally and to devices for obstructing the ear canal to reduce the noise heard by a user and more particularly for filtering noise to enable discernment of speech in a noisy environment.

BACKGROUND OF THE INVENTION

In recent years with the advent of urban living, noise pollution has become an increasingly significant problem. Loud noise is also a problem in the workplace where high levels of machinery noise can cause damage to the ears. Indeed, to protect workers there exists in many countries legislation requiring employers to provide ear protection for their employees.

Noise pollution, whilst being an irritation, is also a cause of hearing loss when the ears are either subjected to a single loud noise or are repeatedly subjected to levels of noise above a safe maximum.

Ear protection has traditionally taken the form of earplugs constructed of plastic, foam, silicone or wax. All of these tend to have disadvantages and are of varying effectiveness in attenuating noise. For example, hard plastic plugs tend to be particularly uncomfortable as they press on the ear canal and concha when in place whereas wax plugs can end up being irretrievably pushed into the ear, requiring removal by a physician. All earplugs currently suffer from the drawback of causing a pressure differential between the atmosphere and the inner ear which leads to discomfort due to the sealing or substantial sealing effect that they have on the ear canal.

Discomfort and inability to hear conversation cause persons to remove their earplugs or neglect to wear them at all with consequences such as irritation, deafness and liability to employers. Further, constant removal and re-insertion of the ear-lug is a cause of contamination, especially in the work place, causing such problems as ear infections.

Reference is now made to FIG. 1A where there is shown a diagram of a prior art earplug, as described in U.S. Pat. No. 3,872,559 to Leight. The earplug consists of a generally cylindrical member, 10, having a body portion 12, a conical end portion 14 at one end of the body and a hollow, flared section 16 at the other end of the body 12. The plug is filled with material 18, for reducing the noise level. Apertures in the end portion 14 and in hollow, flared section 16 allow the foam to breathe. Earplug 10 is designed to fit snugly into the ear canal, its flared and forming a seal over the entrance hole to the ear.

FIG. 1B shows a further example of a prior art earplug as described in U.S. Pat. No. 4,094,315 to Leight, comprising an earplug which substantially seals the ear canal. The latter earplug is semi-rigid and is inserted relatively deeply into the ear canal in order to produce a maximum deadening and sound absorbing effect on the incoming sound.

This above-mentioned prior art plugs suffer from the drawbacks of causing discomfort due to the substantial sealing effect that they have on the ear canal. They are also rigid or semi-rigid causing discomfort due to pressure on the ear-canal or the concha of the ear. Furthermore, the earplugs tend to reduce all sounds and prevent conversation from being heard.

SUMMARY OF THE INVENTION

An object of the present invention is to provide an earplug which overcomes the limitations and disadvantages of prior earplugs.

A further object of the present invention is to provide an earplug which blocks noise without substantially sealing the ear canal and causing discomfort to the wearer;

A further object of the present invention is to provide an earplug which allows conversation to be conducted whilst inserted in the ear while at the same time blocking out "load" noise and uncomfortable sounds.

Thee is thus provided, in accordance with a preferred embodiment of the present invention, an earplug which has a first cylindrical element made of a first material and a second element which fits over the first cylindrical element made of a second material. The first element is inserted into an ear canal and is substantially convex in shape. The second element is open at one end and closed at its other end. The first element has at least one aperture. The second element has at least one aperture in the carrier of its closed end.

Furthermore, in accordance with a preferred embodiment of the present invention the aperture in the first cylindrical element is approximately in the center of its closed end.

Further, in accordance with a preferred embodiment of the present invention the aperture in the first cylindrical element is on the cylindrical surface of the first cylindrical element. The aperture is adjacent to the connection between the two elements.

In accordance with a further preferred embodiment of the present invention there is provided an earplug, which has a first cylindrical element and a second element which fits into the first element. The first cylindrical element is constructed of a first material and is open at one end. It is substantially convex in shape at one end which is inserted into an ear canal. The first cylindrical element has air circulation means. The second element is made of a second material and is tapered, the narrower end fitting into the first cylindrical element.

In a preferred embodiment of the present invention the air circulation means consists of two apertures. The first aperture is approximately in the carrier of the closed convex end of the cylindrical element and the second aperture is formed in the cylindrical surface of the cylindrical element adjacent to the connecting juncture between the two elements.

In a further preferred embodiment of the present invention, the air circulation means consists of an aperture and a conduit. The aperture is approximately in the center of the closed convex end of the cylindrical element and the conduit is formed approximately through the center of the second element.

The second element includes a generally annular element having a projecting annular rib integrally formed thereto, the nib being substantially located at the center of the annular element. The second element may further have at least one aperture formed within the projecting annular nib. Alternatively, the second element includes a generally annular element having an annular groove formed therein or a part of the ring removal.

Furthermore, in a preferred embodiment of the present invention the second material is softer than the first material. Alternatively, the same materials maybe used. The thickness of the material may also vary.

In a preferred embodiment of the present invention there is provided an earplug consisting of a first cylindrical element which is open at both ends to which is attached a second and third element. The first cylindrical element has a narrow lip around the outer surface of one open end, no such lip at its second end and is constructed of a first material. The second element is constructed of a second material and is open at one narrow end and closed at the other wide end for insertion into an ear canal. The second element is tapered from a first wide end to a second narrow end. The third element is constructed of a third material and is open at one end and closed at its other convex end. The diameter of the open ends of the second and third elements is greater than the diameter of the lip-bearing open end of the first cylindrical element and the converse end of the first cylindrical element respectively to allow both to respectively fit tightly over the open ends of the first cylindrical element to form connecting junctures. The second element contains an aperture approximately in the center of its wide end. The third element contains an aperture approximately in the center of its closed convex end.

In a further preferred embodiment of the present invention the aperture in the third element is replaced by an aperture on the cylindrical surface of the first cylindrical element adjacent to the join between the first and third elements.

In a further preferred embodiment of the present invention the second and third materials are softer than the first material.

In a preferred embodiment of the present invention there is provided an earplug which consists of a cylindrical element. The cylindrical element is constructed of a rigid material and has a proximate and distal end each having a substantially convex shape. The proximate end is for insertion into an ear canal. The cylindrical element has an aperture or apertures in its proximate end and a second aperture on the cylindrical surface of the cylindrical element distal from the first aperture or apertures.

In a further preferred embodiment of the present invention the second aperture is formed approximately in the center of the distant and the cylindrical element.

Furthermore in accordance with a preferred embodiment of the present invention, the element includes sound absorbing material proximate to the convex end inserted into the ear.

In addition, in accordance with a preferred embodiment of the present invention, the earplug may contain protruding elements integrally formed with the element distal from the ear to allow for easier grasp of the earplug when being inserted and removed from the ear.

BRIEF DESCRIPTION OF THE DRAWINGS

The present invention will be understood and appreciated more fully from the following detailed description taken in conjunction with the appended drawings in which:

FIGS. 4A, 4B, 4C, 4D, 4E and 4F are schematic illustrations of bi-elemental earplugs according to further preferred embodiments of the present invention;

DETAILED DESCRIPTION OF THE PRESENT INVENTION

Figure 1A:
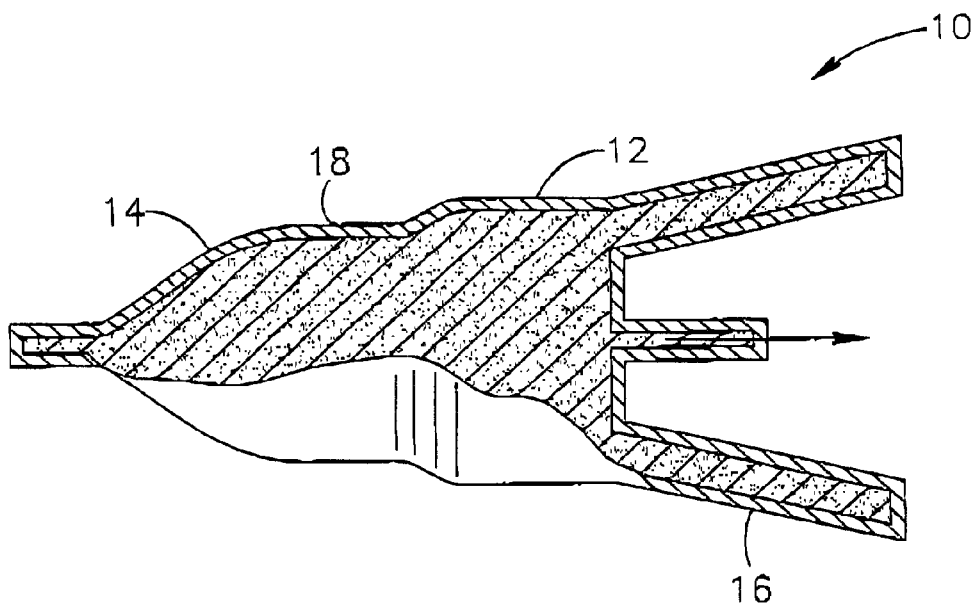
FIGS. 1A and 1B are schematic illustrations of prior art earplugs.
Figure 1B:
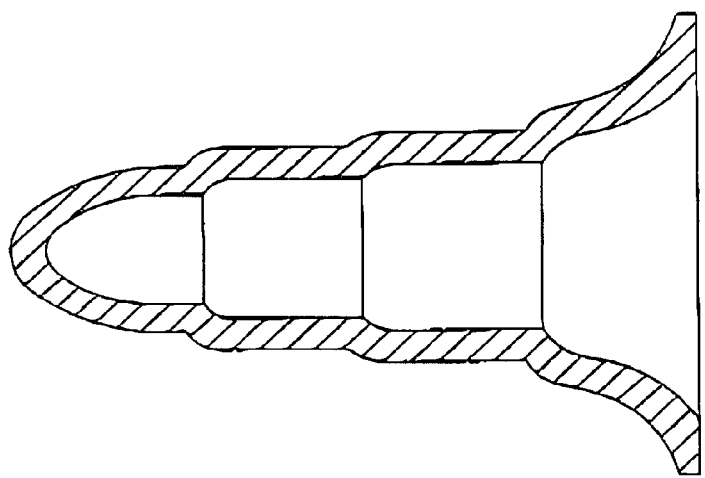
Figure 2:
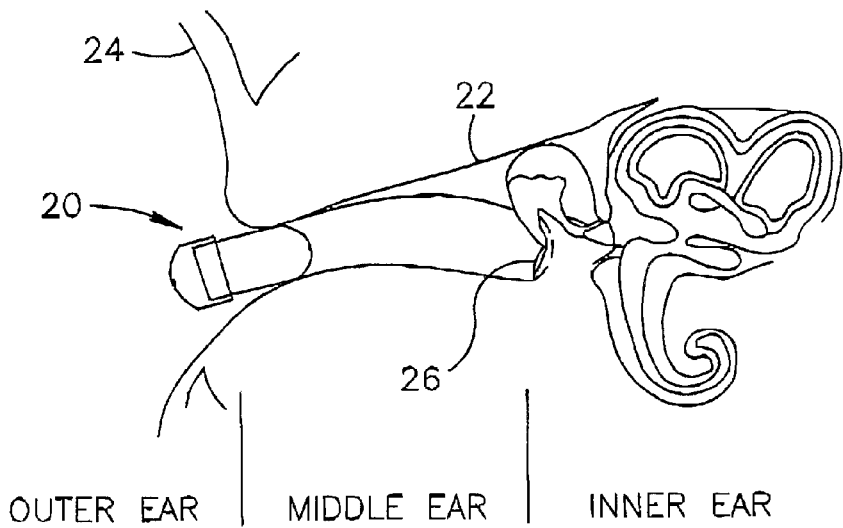
FIG. 2 is a schematic illustration of an earplug inserted into an ear according to a preferred embodiment of the present invention.

Reference is now made to FIG. 2 which schematically illustrates an earplug, 20, constructed according to a preferred embodiment of the present invention, inserted into the ear-canal 22 of the outer ear (or concha) of a user. Earplug 20 is positioned in ear-canal 22, to prevent sound from reaching eardrum, 26.

Figure 3A:
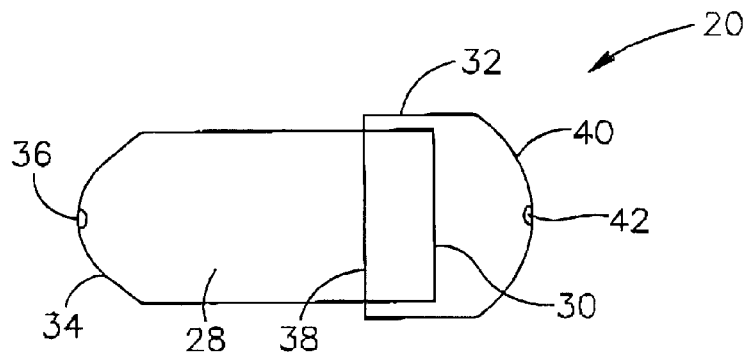
FIGS. 3A and 3B are schematic illustrations of bi-elemental earplugs according to preferred embodiments of the present invention.

Reference is now made to FIG. 3A, which schematically illustrates earplug 20 constructed in accordance with a preferred embodiment of the present invention. Earplug 20 comprises a hollow cylindrical member 28, open at one end 30 over which is sealably fitted a second member 32. Earplug 20 is closed at its other end 34 which has substantially convex shape in order to fit into a user's ear.

Hollow cylindrical member 28 is constructed of a non-flexible material such as plastic, polyvinyl chloride, or other similar material. An aperture 36 is formed in the center of the convex end 34 of hollow cylindrical member 28.

Second member 32 is preferably constructed of a soft, pliable material such as latex or silicone. Second member 32 is teat-like having an open end 38 and a closed end 40 which has a substantially convex shape. An aperture 42 is formed in the center of the convex end 40 of second member 32. The diameter of end 38 is such that it can sealably be fitted over open end 30 of member 28 to form a substantially air tight seal.

It will be appreciated by persons knowledgeable in the art that hollow cylindrical member 28 and second member 32 may be constructed from similar materials, and that it is not essential that different materials, as described hereinabove, be used. Thus, for example, in an alternative embodiment, both cylindrical member 28 and second member 32 may be formed from the same material, such as a silicone or other soft, pliable materials.

The combination of aperture 36 in convex end 34 of hollow cylindrical member 28 and aperture 42 in convex end 40 of second member 32 allows for air to circulate within the hollow cylindrical member 28 and thus allows the ear to "breathe" when earplug 20 is inserted therein increasing the comfort of the user. Thus, though the apertures are relatively small, they allow air to enter the earplug 20 and consequently there is an effective equalization of air pressure between the ear, the earplug and the outside environment.

Earplug 20 is inserted into the ear as described hereinabove (FIG. 2) to reduce the noise reaching the user's inner ear. However, the unique construction of earplug 20 also facilitates the discernment of and the engagement in conversation whilst earplug 20 is in place and functioning to block's load noise. This feature prevents the necessity for frequent removal, stopping of work and soiling due to removal. Further, earplug 20 allows the wearer to hear soft noises such as the ring of a telephone from the general background.

Figure 3B:
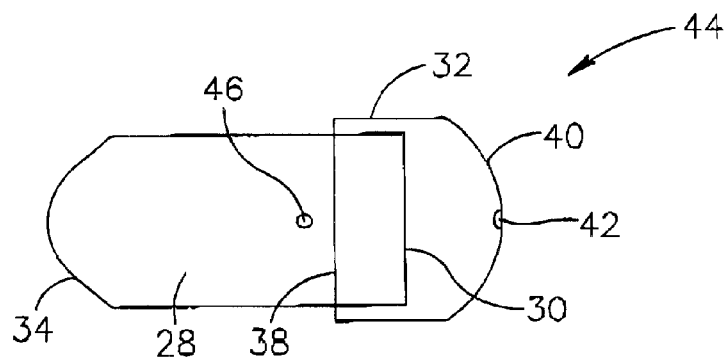

Reference is now made to FIG. 3B, which schematically illustrates an earplug 44, constructed according to a preferred embodiment of the present invention. Elements of this embodiment of the invention which are similar to elements which have been previously described with respect to the preferred embodiment hereinabove, are similarly designated and will not be further described.

Earplug 44 is similar to earplug 20 described hereinabove with respect to FIG. 3A, except that, in the preferred embodiment of FIG. 38, aperture 36 in convex end 34 of hollow cylindrical element 28 (FIG. 3A) is replaced by an aperture 46 on the surface of hollow cylindrical member 28, adjacent to the connecting juncture of hollow cylindrical member 28 and second member 32.

The combination of aperture 46 on the surface of hollow cylindrical member 28 and aperture 42 in convex end 40 of second member 32 allows for air to circulate within the hollow cylindrical member 28 and thus allows the ear to "breathe" when earplug 20 is inserted therein increasing the comfort of the user.

Reference is now made to FIGS. 4A and 4B which schematically illustrate earplugs 46 and 54, respectively, constructed in accordance with further preferred embodiments of the present invention. Similarly elements are similarly numbered.

Earplug 46 comprises a hollow cylindrical member 28, open at one end 30 into which is sealingly fitted a second member 48. Earplug 46 is closed at its other end 34 which has a substantially convex shape in order to fit into a user's ear.

Hollow cylindrical member 28 is constructed of a material such as plastic, polystyrene, polyvinyl chloride, silicone or other similar material. An aperture 36 is formed in the center of the convex end 34 of hollow cylindrical member 28.

Second member 48 is preferably constructed of a soft pliable sound absorbent material, such as rubber, latex or silicone. Second member 48 is preferably tapered from a first wide end 50 to a second narrower end 52. The diameter of element 48 at end 52 is such that it can sealably be inserted into the open end 30 of member 28 to form a substantially air tight seal. A conduit 53 is formed through the center of second member 48.

The combination of aperture 36 in convex end 34 of hollow cylindrical member 28 and the conduit 58 through second member 48 allows for air to circulate within the hollow cylindrical member 28 and thus allows the ear to "breathe", when earplug 46 is inserted therein.

Reference is now made to FIG. 4B, which is similar to FIG. 4A except that conduit 53 through second member 48 (FIG. 4A) is replaced by an aperture 56 on the surface of hollow cylindrical member 28. Aperture 56 is adjacent to the connecting juncture of hollow cylindrical member 28 and second member 48 to allow for air to circulate within the hollow cylindrical member 28.

Earplugs 54 and 46 are inserted into the ear as described hereinabove (FIG. 2).

Reference is now made to FIG. 4C, which schematically illustrates a preferred embodiment of an earplug, generally designated 47. Elements of this embodiment of the invention which are similar to elements which have been previously described with respect to the preferred embodiment hereinabove, are similarly designated and will not further be described. FIG. 4C is similar to FIG. 4A comprises a hollow cylindrical member 28, open at one end 30 into which is sealingly fitted a second member 59.

Cylindrical member 28 has a curved shape to ease of insertion into the ear canal and second member 59 having a plurality of winglets 57 integrally molded thereto. Winglets 57 allow for an easier grasp of the earplug and the ease of removal of earplug 47 from the ear-canal. A conduit 61 through second member 59 allows for air to circulate within the hollow cylindrical member 28 and allows the ear to "breathe". Second member 59 comprises a generally annular element having a nib integrally formed and projecting from the middle of the annular element. Second member 59 has a "L"-shaped configuration when viewed in section.

In an alternative embodiment illustrated in FIG. 4F, the projecting nib (61") extends into the air space of cylindrical member 28. A plurality of apertures may be formed within the projecting nib (61").

As described hereinabove, hollow cylindrical member 28 may be formed from any suitable material, such as silicone or other soft, pliable material. The second member 59 (having three winglets 57) may also be formed of the same material as hollow cylindrical member 28. Alternatively, second member 59 may be constructed from any other suitable material.

Reference is now made to FIG. 4D, which schematically illustrates an alternative preferred embodiment of the earplug 47, of FIG. 4D is similar to FIG. 4C, described hereinabove, comprising a hollow cylindrical member 28, open at one end 30 into which is sealingly fitted a second member 59. Cylindrical member 28 has a curved shape for ease of insertion into the ear canal and second member 59' having a plurality of winglets 57, integrally molded thereto.

The second member 59' is similar to second member 59 of FIG. 4C except for its shape. Thus, second member 59' (FIG. 4D) comprises a generally annular element having a central portion removed. Conduit 61' is thus smaller than conduit 61 of second member 59 (FIG. 4D).

Reference is now made to FIG. 4E which schematically illustrates a further preferred embodiment of an earplug generally designated 49. Elements of this embodiment of the invention which are similar to elements which have been previously described with respect to the preferred embodiment hereinabove, are similarly designated and will not further be described. FIG. 4E is similar to FIG. 4A comprises a hollow cylindrical member 28, open at one end 30 into which is sealingly fitted a second member 48.

Cylindrical member 28 further contains a plug of material 63 constructed of a material such as plastic, polystyrene, polyvinyl chloride silicone or other similar material. A conduit 65 is formed through the center of second member 63, to allow air to circulate therewithin. Plug 65 may take the form of a separate cap which forms convex end 34 of earplug 49. Aperture 36 (of FIG. 4A) is replaced by a conduit 65, similar to conduit 53 to facilitate the circulation of air as described hereinabove.

Preferably, cylindrical member 28 is constructed of silicone and second member 48 is constructed of rubber or silicone.

It will be appreciated that any of the embodiments described herein may also contain sound absorbing materials in their ends. The amount and type of sound absorbing materials may be varied to suit different sound-absorbing requirements of applications of earplugs.

Figure 5A:
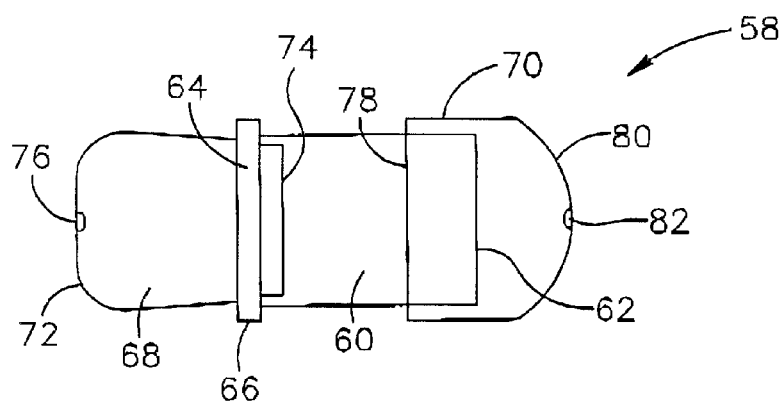
FIGS. 5A and 5B are schematic illustrations of tri-elemental earplugs according to preferred embodiments of the present invention.
Figure 5B:
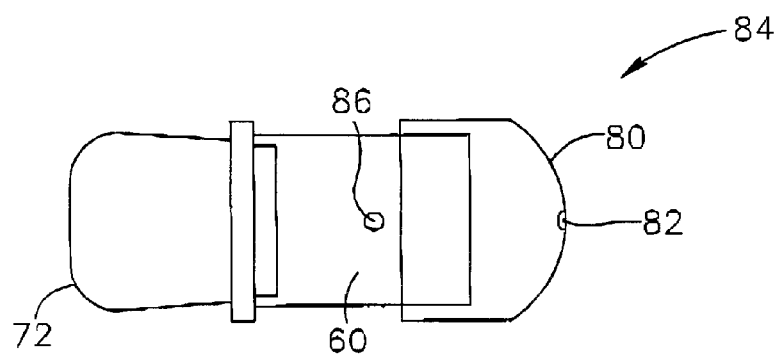

Reference is now made to FIGS. 5A and 5B which schematically illustrate earplugs 58 and 84, respectively, constructed in accordance with further preferred embodiments of the present invention. Similar elements are similarly numbered.

Earplug 58 comprises a hollow cylindrical element 60 open at both ends 62 and 64. Hollow cylindrical element 60 has a lip 66, formed around the outer surface of element 60, at end 64. Sealingly fitted into end 64 is a second member 68 and sealingly fitted over end 62 is a third member 70.

Hollow cylindrical member 60 is constructed of a non-flexible material such as plastic, polystyrene, polyvinyl chloride or other similar material.

Second member 68 is manufactured from a material which is softer than that of hollow cylindrical member 60 and preferably constructed of a soft pliable material such as rubber or latex. Second member 68 is hollow and tapered from a first wide end 72 to a second narrower end 74. The diameter of element 68 at end 74 is such that it can be sealably inserted into the open end 64 of member 60 to form a substantially air tight seal. An aperture 76 is formed in the center of the wide end 72 of second member 68. Earplug 58 is inserted into the ear, second member 68 first, as shown hereinabove (FIG. 2).

Third member 70 is manufactured from a material which is softer than that of hollow cylindrical member 60 and preferably constructed of a soft, pliable material such as latex. Third member 70 is teat-like having an open end 8 and a closed end 80 which has a substantially convex shape. An aperture 82 is formed in the center of the convex end 80 of third member 70.

The diameter of end 78 is such that it can sealably be fitted over open end 62 of member 60 to form a substantially airtight seal.

The combination of aperture 76 in wide end 72 of second member 68 and aperture 82 in the center of convex end 80 of third member 70 allows for air to circulate within the hollow cylindrical member 60 and thus allows the ear to "breathe" when earplug 58 is inserted therein.

It will be appreciated by persons knowledgeable in the art that hollow cylindrical member 60, second member 68 and third member 70 may be constructed from similar materials, and that it is not essential that different materials, as described hereinabove, be used. Thus, for example, in an alternative embodiment, the three members (cylindrical member 60, second member 68 and third member 70) may be formed from the same material, such as a silicone or other soft, pliable materials. In the preferred embodiment of FIG. 5B, aperture 76 in wide end 72 of second member 68 (FIG. 5A) is replaced by an aperture 86, on the surface of hollow cylindrical member 60, approximately two thirds of the distance from wide end 72 to convex end 80 to allow for air to circulate within the hollow cylindrical member 60.

Figure 6A:
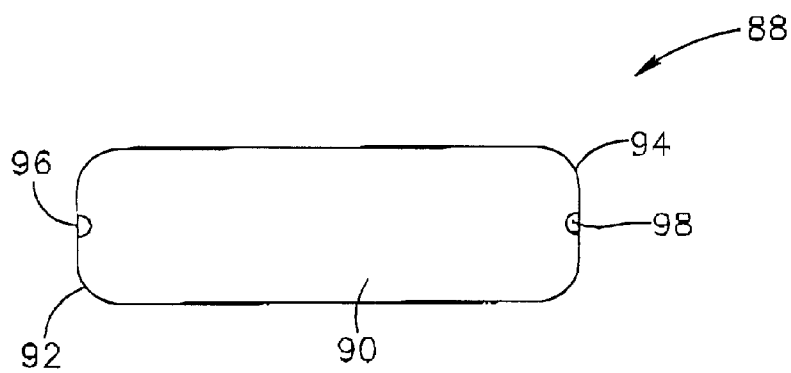
FIGS. 6A and 6B are schematic illustrations of unitary earplugs according to preferred embodiments of the present invention.
Figure 6B:
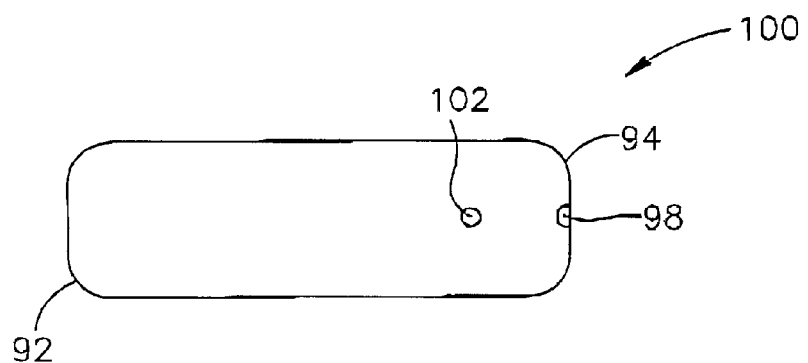

Reference is now made to FIGS. 6A and 6B, which schematically illustrate earplugs 68 and 100, respectively, constructed in accordance with further preferred embodiments of the present invention. The embodiments of FIGS. 6A and 6B are similar (Similar elements are similarly numbered) comprising a single element, referenced 90.

Earplug 68 comprises a hollow cylindrical member 90, closed at both ends 92 and 94 which are substantially convex in shape in order to fit into a user's ear. Hollow cylindrical member 90 is constructed of a non-flexible material such as plastic, polyvinyl chloride or other similar material. Apertures 96 and 98 are formed in the center of ends 92 and 94. Apertures 96 and 98 allow for air to circulate within the hollow cylindrical member 90 and thus allows the ear to breather when earplug 88 is inserted therein. Earplug 68 is inserted into the ear as described hereinabove (FIG. 2).

The preferred embodiment of FIG. 6B, comprises a hollow cylindrical member 90 with an aperture 102 on the surface of hollow cylindrical member 90, approximately two thirds of the distance from end 92 to end 94 (in place of aperture 96 in FIG. 6A) end an aperture 98 at end 94 of hollow cylindrical member 90.

An experiment to measure the effectiveness of the embodiments of the present invention has been formulated. An experimenter actuates a source of sound in a closed area and measures the sound level with a decibel meter. The experimenter then blocks his ears with an embodiment of the earplug to be evaluated. For each blocking in accordance with the last procedure for the embodiment the experimenter then unblocks his ears and walks to a distance from the source of the noise where the sound level is the same as it was within the closed area with the earplug in situ. The results of such as experiment performed for the embodiment of FIG. 4C of the earplug are shown in the table below.

| Without Earplug | With Earplug | % Improvement |
| --- | --- | --- |
| 105 dB | 75 dB | 28% |
| 120 dB | 80 dB | 33% |

As can be seen from the above, the percentage improvement is significant. Moreover, the actual level of noise is reduced to 80 dB level at highest levels.

As will be appreciated by persons knowledgeable in the art, the various embodiments hereinbefore referred to are given by way of example only and do not in any way limit the present invention. For example, though the above embodiments have been described with respect to a hollow cylindrical element, the invention is also applicable to element shaving other shapes and configurations, such as generally tapered configuration to suit the shape, of the outer ear. Further, the element need not be entirely hollow provided that air can circulate within it to prevent pressure build-up and discomfort to the user. As long as there is a passage of air from the outside via the earplug to the ear, there is an effective equalization of air pressure which prevents the discomfort of conventional earplugs.

Furthermore, it will be appreciated that though the above embodiments have been described with respect to hollow cylindrical members having an aperture therein, it is possible to achieve sound reduction using a hollow cylindrical member without the aperture, albeit at a lower comfort level.

Those skilled in the art will readily appreciate that various charges, modifications and variations maybe applied to the preferred embodiments without departing from the scope of the invention as defined in and by the appended claims.

What is claimed is:

1. An earplug comprising:
   a first cylindrical element, constructed of a first material, open at one end and having a substantially convex closed shape at its other end, for invention into the outer ear canal; and
   a second element constructed of a second material, said second element being tapered from a first wide end to a second narrower end; wherein the diameter of said narrower end of said second element is less than the diameter of the open end of said first cylindrical element to allow it to fit tightly into the open end of said first cylindrical element to form a connecting junction therewith;
   wherein said first and second elements have first and second air circulation means respectively.

2. The earplug according to claim 1, wherein said first air circulation means comprises a first aperture formed substantially in the center of said closed convex end of said cylindrical element and a second aperture formed in the cylindrical surface of said cylindrical element, adjacent to said connecting juncture.

3. The earplug according to claim 1, wherein said first air circulation means comprises a first aperture formed substantially in the center of said closed convex end of said cylindrical element.

4. The earplug according to claim 1, wherein said second material is softer than said first material.

5. The earplug according to claim 1, wherein said second material and said first material are similar.

6. The earplug according to claim 1, wherein said second element comprises a plurality of protruding elements integrally formed with said second element.

7. The earplug according to claim 1, wherein said second air circulation means comprises a conduit formed substantially through the center thereof.

8. The earplug according to claim 7, wherein said second element comprises a generally annular element having a projecting annular nib integrally formed thereto, wherein said nib is substantially located at the center of said annular element.

9. The earplug according to claim 8, wherein said second element further comprises at least one aperture formed within said projecting annular nib.

10. The earplug according to claim 7, wherein said second element comprises a generally annular element having an annular groove formed therein.

11. The earplug according to claim 1, wherein the air pressure within said first and second elements is equal to the air pressure of the air surrounding the earplug and within the ear.

12. The earplug according to claim 1 wherein said first cylindrical element comprises sound absorbing material inserted proximate to said convex end said sound absorbing a conduit formed therethrough.

13. An earplug comprising:
a first cylindrical element, constructed of a first material, open at one end and having a substantially convex shape at its other end for insertion into the outer ear canal, said first cylindrical element having at least one aperture formed therein;
a second element constructed of a second material, said second element open at one end and closed at its other end, said second element having at least one aperture formed substantially in the carrier of its closed end;
wherein the diameter of the open end of said second element is greater than the diameter of the open end of said first cylindrical
element to allow it to fit tightly over the open end of said first cylindrical element to form a connecting juncture therewith.

14. The earplug according to claim 13, wherein the air pressure within said first and second elements is equal to the air pressure of the air surrounding the earplug and within the ear.

15. The earplug according to claim 13, wherein said at least one aperture of said first cylindrical element is an aperture formed substantially in the center of said closed convex end.

16. The earplug according to claim 13, wherein said at least one aperture of said first cylindrical element is an aperture on the cylindrical surface thereof adjacent to said corresponding juncture.

17. The earplug according to any of claims 13–16, wherein said second material is softer than said first material.

18. The earplug according to any of claims 13–16, wherein said second material and said first material are similar.

19. The earplug according to claim 13 wherein said first cylindrical element comprises sound absorbing material inserted proximate to said convex end, said sound absorbing material having a conduit formed therethrough.

20. An earplug comprising:
a first cylindrical element, constructed of a first material, open at both ends, a first end having a narrow lip formed around the outer surface of one open end;
a second element constructed of a second material, said second element open at one narrow end and closed at its other wide and for insertion into an ear canal and tapered from said first wide end to said second narrow end;
a third element constructed of a third material, said third element open at one end and closed at its other convex end;
wherein the diameter of each of said open ends of said second and third elements is greater than the diameter of said lip-bearing open end of said first cylindrical element and said converse end of said first cylindrical element respectively to allow both to respectively fit tightly over the open ends of said first cylindrical element to form connecting junctures therewith; and
wherein said second element contains an aperture substantially in the center of its wide end and said third element contains at least one aperture.

21. The earplug according to claim 20, wherein the air pressure within said first, second and third elements is equal to the air pressure of the air surrounding the earplug and within the ear.

22. The earplug according to claim 20, wherein said at least one aperture in said third element is an aperture formed substantially in the center of said closed convex end.

23. The earplug according to claim 20, wherein said at least one aperture in said third element is an aperture on the cylindrical surface of said first cylindrical element adjacent to said connecting juncture between said first and said third elements.

24. The earplug according to any of claims 20–23, wherein said second and said third materials are softer than said first material.

25. The earplug according to any of claims 20–23, wherein said first, second and third materials are formed from the same material.

26. The earplug according to any of claims 20–23, wherein the thickness of said first, second and third materials are different each from the other.

27. An earplug comprising:
a cylindrical element, constructed of a rigid material, having a proximate and distal end, each having a substantially convex shape, said proximate end for insertion into an ear canal; and
wherein said cylindrical element comprises at least one aperture formed in the proximate end thereof and a second aperture formed therein to allow air to circulate.

28. The earplug according to claim 27, wherein the air pressure within said element is equal to the air pressure of the air surrounding the earplug and within the ear.

29. The earplug according to claim 27, wherein said second aperture is an aperture on the cylindrical surface of said cylindrical element distal from said at least first aperture.

30. The earplug according to claim 27, wherein said second aperture is formed substantially in the center of said distal end.

31. The earplug according to any of claims 27–30, wherein said proximate end comprises sound absorbing material and said sound absorbing a conduit formed therethrough.

* * * * *